United States Patent
Gordon

(10) Patent No.: US 11,517,721 B2
(45) Date of Patent: Dec. 6, 2022

(54) INTERVENTIONAL TOOL DELIVERY DEVICES, SYSTEMS AND MELHODS

(71) Applicant: Radux Devices, LLC, Omaha, NE (US)

(72) Inventor: Gregory Gordon, Omaha, NE (US)

(73) Assignee: Radux Devices, LLC, Maple Grove, MN (US)

( * ) Notice: Subject to any disclaimer, the term of this patent is extended or adjusted under 35 U.S.C. 154(b) by 479 days.

(21) Appl. No.: 16/786,597

(22) Filed: Feb. 10, 2020

(65) Prior Publication Data

US 2020/0188638 A1 Jun. 18, 2020

Related U.S. Application Data

(62) Division of application No. 15/459,770, filed on Mar. 15, 2017, now Pat. No. 10,556,094.

(51) Int. Cl.
*A61M 25/06* (2006.01)
*A61M 39/10* (2006.01)
*A61M 39/06* (2006.01)
*A61M 39/22* (2006.01)
(Continued)

(52) U.S. Cl.
CPC .... *A61M 25/0662* (2013.01); *A61M 25/0097* (2013.01); *A61M 25/02* (2013.01); *A61M 39/06* (2013.01); *A61M 39/10* (2013.01); *A61M 39/223* (2013.01); *A61M 2025/024* (2013.01); *A61M 2025/0206* (2013.01); *A61M 2025/028* (2013.01); *A61M 2025/0266* (2013.01); *A61M 2039/1077* (2013.01); *A61M 2039/229* (2013.01)

(58) Field of Classification Search
CPC .......... A61M 25/0662; A61M 25/0097; A61M 25/02; A61M 39/06; A61M 39/10; A61M 39/223; A61M 2025/0206; A61M 2025/024; A61M 2025/0266; A61M 2025/028; A61M 2039/1077; A61M 2039/229; A61M 25/0041; A61M 2210/012; A61M 25/09041; A61M 25/09
See application file for complete search history.

(56) References Cited

U.S. PATENT DOCUMENTS

| 3,853,126 | A | 12/1974 | Schulte |
| 3,998,222 | A | 12/1976 | Shihata |
| 4,029,103 | A | 6/1977 | McConnell |

(Continued)

FOREIGN PATENT DOCUMENTS

CN  106413802  2/2017

OTHER PUBLICATIONS

Dr. Gregory Gordon, Radux Devices, LLC, "Demo Day 2013: Radux," YouTube [online], Published on Nov. 26, 2013, Retrieved Apr. 18, 2018, Retrieved from the Internet: <URL: https://www.youtube.com/watch?v=SsZhtA7heJE>, 2 pages.

(Continued)

*Primary Examiner* — Amber R Stiles
(74) *Attorney, Agent, or Firm* — Fish & Richardson P.C.

(57) ABSTRACT

In general, medical sheath systems that include a curved support sheath are described. In one embodiment, the support sheath includes a curved tube includes a distal portion fixed in an orientation perpendicular to the proximal end during advancement of an interventional tool through the support sheath.

20 Claims, 10 Drawing Sheets

(51) Int. Cl.
*A61M 25/02* (2006.01)
*A61M 25/00* (2006.01)

(56) References Cited

U.S. PATENT DOCUMENTS

| | | | |
|---|---|---|---|
| 4,316,461 A | 2/1982 | Marais et al. |
| 4,453,933 A | 6/1984 | Speaker |
| 4,585,435 A | 4/1986 | Vaillancourt |
| 4,840,613 A | 6/1989 | Balbierz |
| 4,850,954 A | 7/1989 | Charvin |
| 4,865,586 A | 9/1989 | Hedberg |
| 4,976,698 A | 12/1990 | Stokley |
| 5,031,775 A | 7/1991 | Kane |
| 5,188,608 A | 2/1993 | Fritts |
| 5,407,434 A | 4/1995 | Gross |
| 5,443,460 A | 8/1995 | Miklusek |
| 5,538,513 A | 7/1996 | Okajima |
| 5,647,859 A | 7/1997 | Lampropoulos et al. |
| 5,902,274 A | 5/1999 | Yamamoto et al. |
| 5,916,199 A | 6/1999 | Miles |
| 5,947,931 A | 9/1999 | Bierman |
| 5,989,223 A | 11/1999 | Chu et al. |
| 6,001,081 A | 12/1999 | Colien |
| 6,113,577 A | 9/2000 | Hakky et al. |
| 6,179,828 B1 | 1/2001 | Mottola |
| 6,193,726 B1 | 2/2001 | Varney |
| 7,198,066 B2 | 4/2007 | Kagenow |
| 7,553,326 B2 | 6/2009 | Sweet |
| 7,571,744 B2 | 8/2009 | Zia |
| 8,911,396 B2 | 12/2014 | Gordon |
| 9,126,018 B1 | 9/2015 | Garrison |
| 9,585,691 B2 | 3/2017 | Gordon |
| 2001/0053895 A1 | 12/2001 | Vaillancourt |
| 2002/0087108 A1 | 7/2002 | Maginot et al. |
| 2002/0107479 A1 | 8/2002 | Bates et al. |
| 2002/0168618 A1 | 11/2002 | Anderson et al. |
| 2004/0087905 A1 | 5/2004 | Breznock et al. |
| 2004/0147877 A1 | 7/2004 | Heuser |
| 2004/0153021 A1 | 8/2004 | Osborne et al. |
| 2005/0033238 A1 | 2/2005 | Cope et al. |
| 2005/0113799 A1 | 5/2005 | Lenker |
| 2005/0165364 A1 | 7/2005 | DiMatteo |
| 2005/0209584 A1 | 9/2005 | Rome |
| 2005/0234405 A1 | 10/2005 | Dikeman et al. |
| 2006/0009737 A1 | 1/2006 | Whiting et al. |
| 2006/0047266 A1 | 3/2006 | Elkins et al. |
| 2006/0074398 A1 | 4/2006 | Whiting et al. |
| 2006/0084927 A1 | 4/2006 | Formichi |
| 2006/0129091 A1 | 6/2006 | Bonnette et al. |
| 2006/0129112 A1 | 6/2006 | Lynn |
| 2006/0129134 A1 | 6/2006 | Kerr |
| 2006/0155247 A1 | 7/2006 | Lampropoulos et al. |
| 2007/0161956 A1 | 7/2007 | Heuser |
| 2007/0167901 A1 | 7/2007 | Herrig et al. |
| 2007/0225680 A1 | 9/2007 | Biggins |
| 2008/0171944 A1 | 7/2008 | Brenneman et al. |
| 2008/0195046 A1 | 8/2008 | Altman |
| 2009/0306574 A1 | 12/2009 | Kopperschmidt |
| 2010/0030162 A1 | 2/2010 | Cremascoli et al. |
| 2012/0071821 A1 | 3/2012 | Yu |
| 2012/0130151 A1 | 5/2012 | Kassab et al. |
| 2012/0209252 A1 | 8/2012 | Nikitina et al. |
| 2013/0006163 A1* | 1/2013 | Gordon .......... A61M 25/01 604/8 |
| 2014/0074123 A1 | 3/2014 | Voss et al. |
| 2014/0343531 A1 | 11/2014 | Larkin |
| 2015/0105752 A1 | 4/2015 | Gordon et al. |
| 2015/0112242 A1 | 4/2015 | Gordon |
| 2017/0072164 A1 | 3/2017 | Gordon et al. |
| 2017/0136218 A1 | 5/2017 | Gordon |
| 2018/0264236 A1 | 9/2018 | Gordon |

OTHER PUBLICATIONS

Dr. Gregory Gordon, Radux Devices, LLC, "Radux Devices." 2015 Society of Interventional Radiology Annual Meeting, SIR Venture Forum, 15 slides, Mar. 3, 2015.

Dr. Gregory Gordon, Radux Devices, LLC, "Radux," YouTube [online], Uploaded on Nov. 15, 2013, Retrieved on Apr. 18, 2018, Retrieved from the Internet: <URL: https://www.youtube.com/watch?v=MduMUiVLxpQ>, 2 pages.

International Search Report and Written Opinion in Appln. No. PCT/US2018/022410, dated May 31, 2018, 13 pages.

Kumru and Mueller., "New Prototypes Designed for Interventional Radiology," UNMC Discover, Aug. 20, 2015, 4 pages.

Extended European Search Report in EP Patent Appln. No. 18768152.3, dated Feb. 21, 2020, 6 pages.

* cited by examiner

INTERVENTIONAL TOOL DELIVERY DEVICES, SYSTEMS AND MELHODS

CROSS-REFERENCE TO RELATED APPLICATIONS

This application claims priority to U.S. application Ser. No. 15/459,770 filed on Mar. 15, 2017, the contents of this aforementioned application being fully incorporated herein by reference.

TECHNICAL FIELD

This document describes devices, systems and methods for delivering an interventional tool in a patient, and in some embodiments, delivering the interventional tool through a curved tube.

BACKGROUND

Radiation protection in the medical field is important, particularly for physicians and healthcare practitioners. Procedures and therapies are often designed to minimize patient exposure while allowing physicians to effectively treat the patient. For example, imaging machines may be designed to decrease patient exposure by implementing lower radiation levels. However, cumulative exposure of physicians and healthcare practitioners may be significant as they often perform multiple treatments in a typical day, and may be increased when a particular treatment requires physicians' hands, for example, to be within a field of radiation. For example, physicians' or healthcare practitioners' hands may be exposed to radiation from fluoroscopic imaging equipment when inserting a catheter in a patient's vessel, or when delivering other instruments, medicines, fluids, or other endovascular devices in a patient's vessel. Various techniques have been used to limit radiation exposure, such as physical barriers including radiation shielding and body wear.

SUMMARY

Some embodiments described herein include systems, devices and methods that facilitate delivery of an interventional tool in a patient. Some exemplary embodiments may include a curved sheath that allows an interventional tool to be handled and delivered into a patient from an ergonomic position of the practitioner. For example, some embodiments of the system provide a practitioner with the benefit of advancing an interventional tool into the patient's left arm while the practitioner is oriented to manipulate the interventional tool primarily using his or her right hand and contemporaneously view all of the patient, the interventional tool, and a medical imaging device within the practitioner's field of view. In particular implementations, an orientation of a portion of the curved sheath may be angled or offset from an insertion axis of a catheter that extends through the skin of a patient. Optionally, the curved support sheath may include an inflexible tube curved to a fixed angle (e.g., 45°, 60°, 90°, 135°, etc.) such that a central axis of a proximal end of the curved support sheath is angled relative to a central axis of a distal end of the curved support sheath. An operator handling the interventional tool at an angle and/or offset from an insertion axis through an access point of a patient may position themselves outside a field of radiation and in an ergonomic posture, and/or operate with a preferred or dominant hand.

Particular embodiments described herein may include a retainer device. The retainer device may be attachable to the support sheath and a surface to maintain a selected position of the support sheath while treatment is performed (e.g., while an interventional tool is advanced through the support sheath). Optionally, the support sheath may be a curvable support sheath bendable between a curved configuration and a straight configuration, and the retainer may maintain the support sheath in a curved configuration. Radiation exposure of an operator may be reduced or minimized while also improving the ergonomic and orthopedic impact upon the practitioner, and the efficiency and effectiveness of interventional procedures improved.

Particular embodiments described herein include a medical sheath system. The system includes a catheter having a distal end, a proximal end, and at least one lumen extending between the distal end and the proximal end. The catheter is configured to receive an interventional tool and comprises a sealable connector at the proximal end having a septum. The system further includes a support sheath having an inflexible tube, a first end having a connector configured to releasably connect with the proximal end of the catheter and a second end having a port configured to receive an interventional tool. The inflexible tube includes a distal portion proximate the first end and a proximal portion proximate the second end, the distal portion fixed in a predetermined orientation perpendicular to the proximal end. The system further includes a retainer configured to secure the support sheath to a surface.

In some implementations, the system may optionally include one or more of the following features. The catheter may be configured for insertion through an opening of a patient's skin, the lumen defining an insertion axis at the opening of the patient's skin. The system may include an extension sheath connected to the second end of the inflexible tube, at least a distal portion of the extension sheath perpendicular to the insertion axis when connected to the inflexible tube. The inflexible tube may be a first inflexible tube, and the sheath system may further include a second inflexible tube, the second inflexible tube including a first end having a connector and a second end including a port configured to receive the interventional tool, the inflexible tube having a distal portion proximate the first end and a proximal portion proximate the second end, the distal portion fixed in a predetermined orientation angled between 60° and 135° relative to the proximal portion. The first inflexible tube and the second inflexible tube may be interchangeably connectable with the catheter. The retainer may include an elastic sleeve configured to secure the tube around an arm or leg. The system may include an adapter configured to join the first end of the catheter to the distal end of the inflexible tube.

Some embodiments described herein include a method of delivering an interventional tool, including positioning a catheter through an access point in a side wall of an anatomical vessel of a patient in the direction of an insertion axis, the catheter having a distal end, a proximal end, and at least one lumen extending between the distal end and the proximal end, the catheter configured to receive an interventional tool; attaching a support sheath including a first end having a connector configured to releasably connect with the proximal end of the catheter and a second end including a port configured to receive an interventional tool, the support sheath having a distal portion proximate the first end and a proximal portion proximate the second end, the distal portion fixed in a predetermined orientation relative to the proximal end when attached to the catheter; and advancing the interventional tool by a practitioner along an advancement direction offset from the insertion axis to deliver an interventional tool within an internal access path through the support sheath, catheter, and anatomical vessel.

In some implementations, the method may optionally include one or more of the following features. The advancement direction may be perpendicular to the insertion axis. The advancement direction may be angled between 60° and 135° relative to the insertion axis. The method may include viewing a display of a monitor and an access point of the patient by the practitioner while advancing the interventional tool, the monitor and the access point within a common field of vision of the practitioner during advancement of the interventional tool. The insertion axis may extend in a direction perpendicular to a viewable display of a monitor, and the proximal portion of the support sheath may be oriented parallel to the viewable display of the monitor, during the step of advancing the interventional tool. The anatomical vessel may be a radial artery. The method may include attaching an adapter to the distal end of the support sheath, and the step of attaching the support sheath to the proximal end of the catheter may include attaching the adapter to the catheter. The interventional tool may include a guidewire. The support sheath may include an inflexible tube. The support sheath may include a curvable tube, and the method may include bending the curvable tube to a curved configuration. The method may include securing the curvable tube in the curved configuration by a retainer. The catheter may be configured to receive an interventional tool and may include a sealable connector at the proximal end having a septum.

Some embodiments described herein include a method of delivering an interventional tool, including positioning a catheter through a patient access point along an insertion axis; attaching a curved support sheath with the catheter; and advancing an interventional tool through the curved support sheath along an advancement direction offset from the insertion axis.

Some embodiments of the devices, systems and techniques described herein may provide one or more of the following advantages. First, some embodiments described herein may reduce physical stress on a physician or healthcare practitioner by facilitating operation from an ergonomic position. For example, a support sheath may be curved to allow an interventional tool to be advanced by an operator in a direction offset from an insertion axis through an access point of the patient. An operator may thus be able to stand upright and/or with their arms in a natural position while advancing the interventional tool (e.g. instead of hunched over the patient in order to operate more closely to the access point).

Second, some embodiments described herein facilitate observation of the patient (e.g. the access point, head, and/or chest, etc.) and a viewable display of a monitor in a common field of vision. For example, a curved support sheath may facilitate operation from a position in which the patient and viewable display are in front of the operator such that the operator's field of vision includes both the patient (e.g. the access point, head, and/or chest, etc.) and the viewable display of a monitor. Orthopedic stress on the operator may be reduced by reducing twisting or rotating motion, and/or not requiring an operator to strain their neck to view the patient or monitor.

Third, some embodiments described herein facilitate manipulation of the interventional tool while operating from a medically advantageous location of the patient. For example, an interventional tool may be advanced from the left side of a patient such that the operator is positioned to manipulate the interventional tool primarily using their right hand, and/or from a right side of a patient such that the operator is positioned to manipulate the interventional tool primarily using their right hand. An operator may thus operate from an access point of the patient selected primarily based on advantages in patient care, such as operating from the left radial artery in a percutaneous coronary intervention, while being less constrained by ergonomic requirements, for example.

Fourth, some embodiments described herein facilitate advancing the interventional tool from a position outside of a strongest location of a radiation field. For example, the interventional tool or other component may be introduced by a physician or healthcare practitioner without requiring their hands to be directly exposed to maximum levels of radiation. Similarly, a patient or healthcare practitioner may work at a greater distance away from imaging equipment, reducing potential exposure to their head, neck, and other body parts.

Fifth, some embodiments facilitate flexibility in the position and direction of advancement of an interventional tool such that treatment times may be reduced and overall patient care improved. For example, the operator's position and dominant hand during operation may be selected with less dependence on the location of a penetration point or the orientation of the insertion axis of a catheter through a patient's skin.

Sixth, some embodiments may improve the control and precision with which an interventional tool may be advanced through the patient. A support sheath including a predetermined curve may impart stability at a location outside of the patient's body, and facilitate advancement in a selected direction.

The details of one or more implementations are set forth in the accompanying drawings and the description below. Other features and advantages will be apparent from the description and drawings, and from the claims.

DESCRIPTION OF DRAWINGS

The present description is further provided with reference to the appended Figures, wherein like structure is referred to be like numerals throughout the several views, and wherein.

DETAILED DESCRIPTION OF ILLUSTRATIVE EMBODIMENTS

Figure 1:
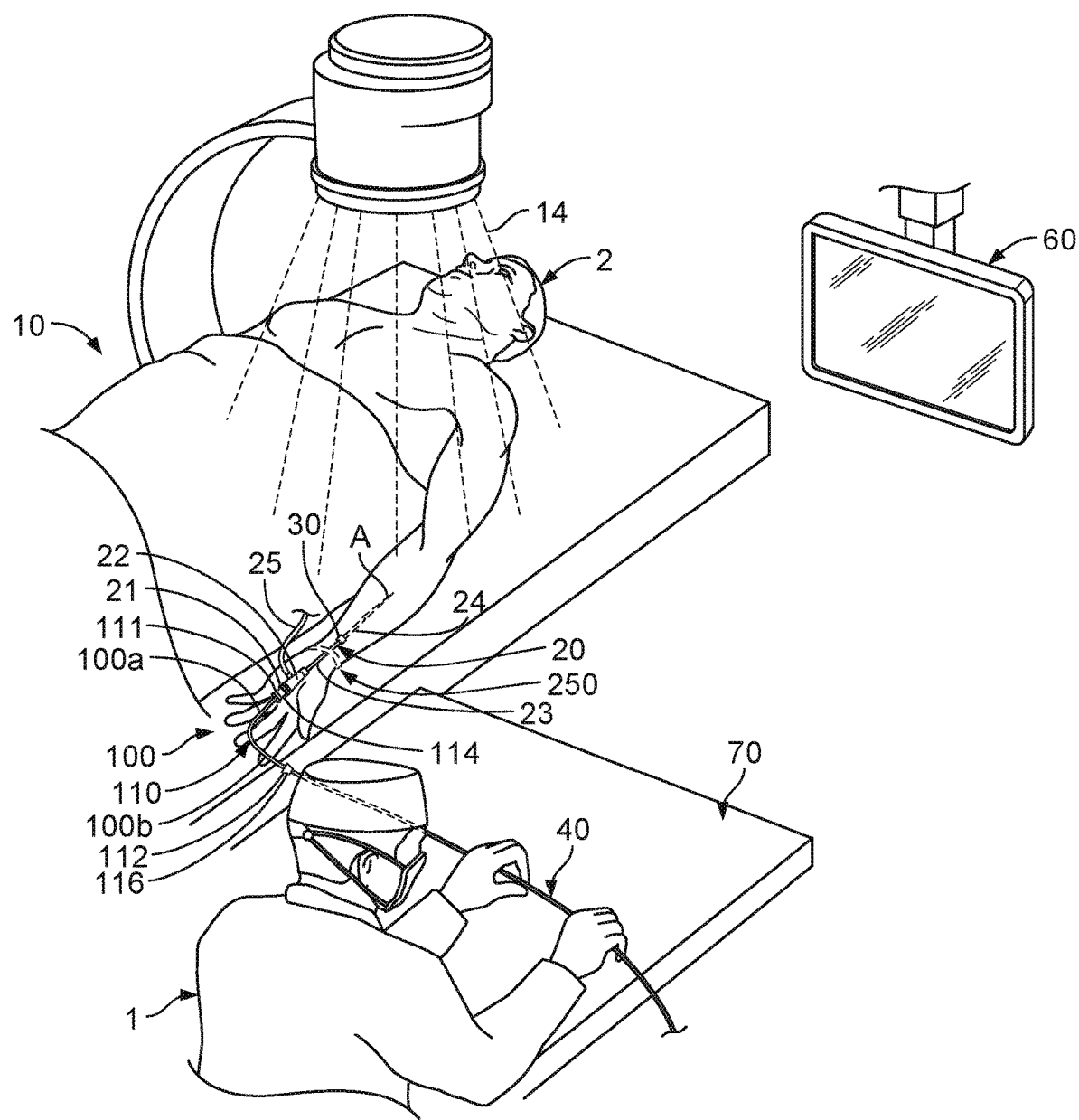
FIG. 1 is a perspective view of an exemplary medical sheath system in use in a medical environment.
Figure 2:
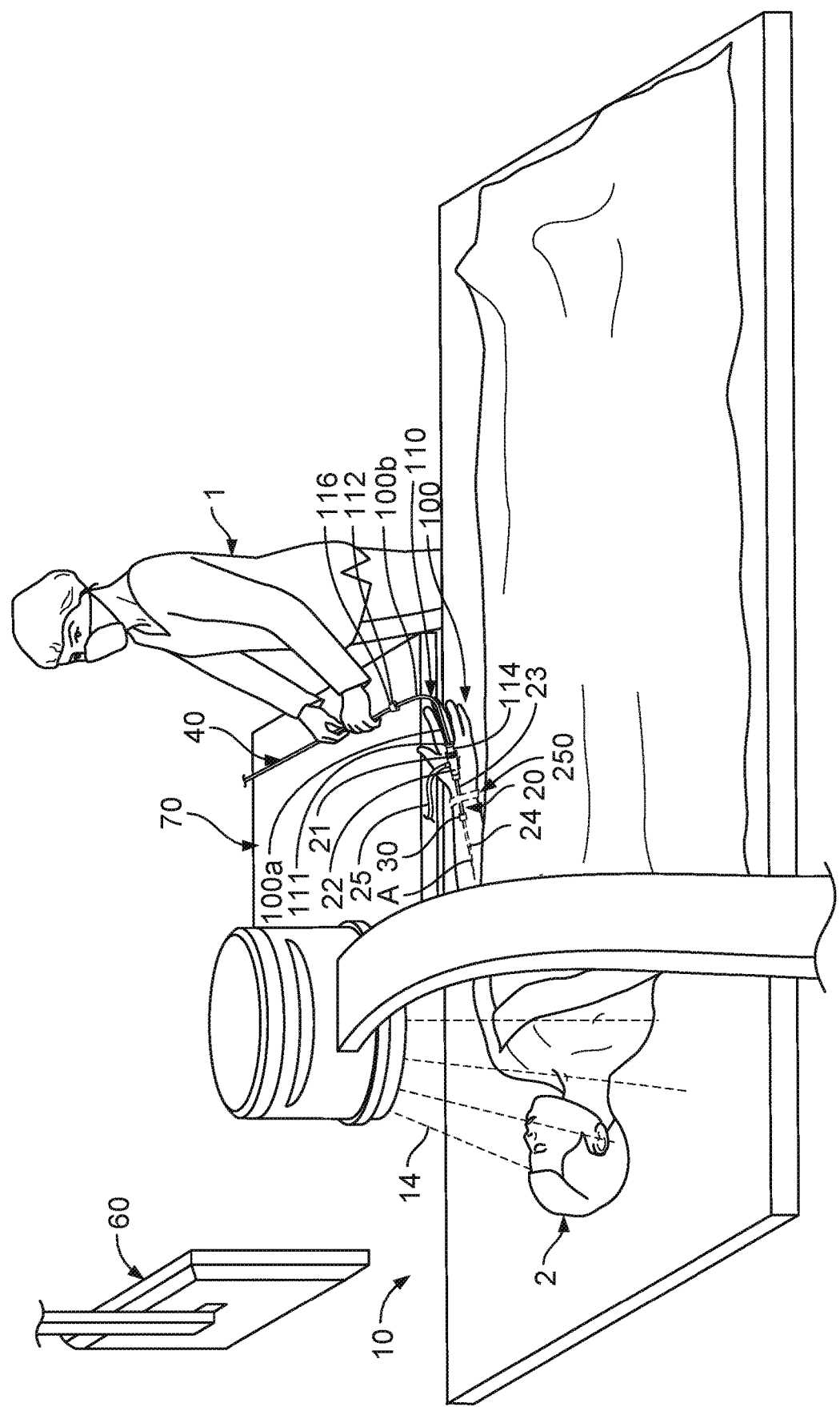
FIG. 2 is another perspective view of the medical sheath system of FIG. 1.
Figure 3:
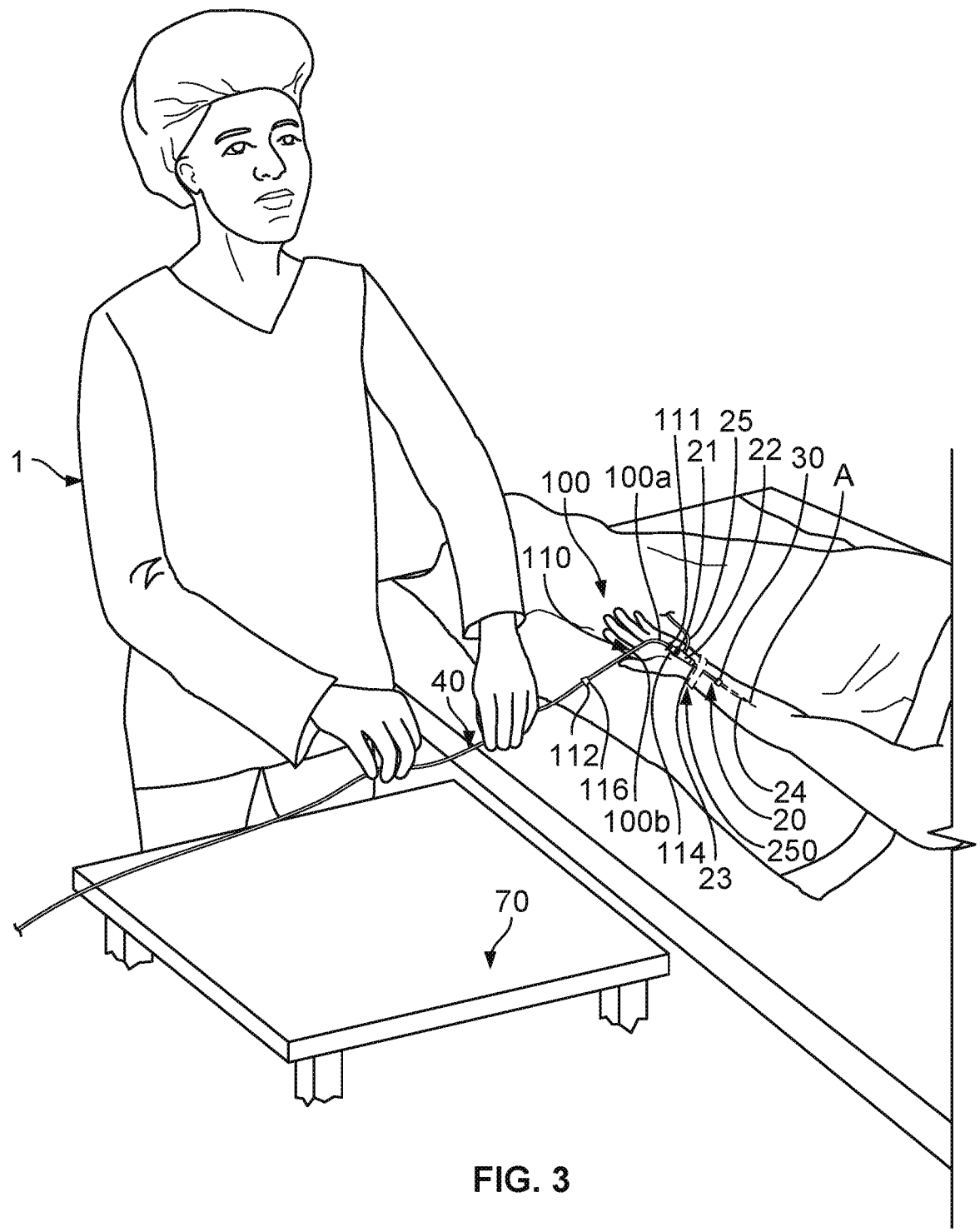
FIG. 3 is another perspective view of the medical sheath system of FIG. 1.

Referring to FIGS. 1-3, an exemplary medical sheath system 10 is shown, including a support sheath 100, a retainer 250 configured to secure a tube 110 of support sheath 100, and optionally, a catheter 20, medical instrument 40, and monitor 60. The support sheath 100 is configured to curve in an orientation that extends an operative location of a practitioner 1 further away from a proximal end 21 of catheter 20 and a radiation field 14 (e.g. caused by a medical imaging system), thereby permitting the practitioner 1 to operate from outside the radiation field, in a different or selected ergonomic position, and/or with a selected dominant hand, for example, while effectively treating a patient 2.

Support sheath 100 includes a first end 111, a second end 112, and a tube 110 extending between the first and second ends 111, 112. Tube 110 includes a distal portion 110a proximate first end 111 and a proximal portion 110b proximate second end 112. Support sheath 100 may include a sealable port 116 that allows medical instrument 40 (e.g. such as an interventional tool) to be passed through tube 110, catheter 20, and into the patient's body at access point 30. In an exemplary embodiment, support sheath 100 is maintained in a stable position entirely outside the patient's body.

Tube 110 may have any suitable length as desired for a particular application or procedure. In an exemplary embodiment, tube 110 has a length between first and second ends 111, 112 between approximately 5 cm and 50 cm, 10 cm and 40 cm, 15 cm and 30 cm, or about 20 cm. Such a length provides a tube 110 that is sufficiently compact to exhibit desirable stability, while sufficiently long to allow flexibility in positioning and configuration such that a physician or healthcare practitioner may operate outside of a direct field of radiation and/or in an ergonomically desirable position. In various exemplary embodiments, sheath assembly 100, and tube 110, are compatible with any suitable French system devices, for example up to 28 French devices, 24 French device, 12 French devices, or between about 5 and 8 French system devices.

In an exemplary embodiment, first end 111 of support sheath 110 includes a connector, such as an adapter 114. Adapter 114 may be removably or permanently joined to first end 111 and includes one or more attachment features configured to couple with catheter 20, for example. Adapter 114 may be removably or permanently attachable to allow communication between tube 110 and catheter 20. In an exemplary embodiment, attachment features include helical threads compatible with one or more introducer sheaths, such as AVANTI+ introducer sheath available from Cordis, the BRITE TIP interventional sheath available from Cordis, the GLIDESHEATH introducer sheath available from Terumo Medical Corporation, SUPER SHEATH introducer sheath available from Boston Scientific Corporation, INPUT introducer sheath available from Medtronic, other introducer sheaths, or components providing vascular access to a patient for the introduction of an interventional tool, medicine, or other component. In various exemplary embodiments, attachment features may include a luer lock connector, bayonet connector, snap connector, or other attachment feature to allow secure connection between adapter 114 and the catheter. In some exemplary embodiments, adapter 114 is configured for attachment to a second end 112 of support sheath 100, such that two or more support sheaths may be connected in series. In an exemplary embodiment, adapter 114 has a widened body to facilitate handling (e.g. a body thicker than tube 110). In some embodiments, the widened body may have a curved surface or one or more features such as texture, ribs, etc. to facilitate handling.

Second end 112 of tube 110 includes a port 116, such as a septum hub port. Port 116 includes at least a first opening for insertion of an interventional tool that may be passed through tube 110, through a component attached at first end 111, and/or into a patient access location, and may include a hemostasis valve. In some exemplary embodiments, port 116 includes a suture connector 117 defining an opening that one or more sutures may be passed through to secure port 116 and second end 112 of tube 110 in a desired location.

Medical sheath system 10 may include a retainer 250 that promotes stability of support sheath 100. For example, retainer 250 may be configured to be attached to a surface to maintain support sheath 100 in a fixed position relative to access point 30. In an exemplary embodiment, retainer 250 includes a clasp having an adhesive pad that can be releasably attached to a surface, such as the patient's skin, garment, surgical draping, etc. Alternatively or additionally, retainer 250 may include an elastic sleeve or band that can be positioned around a body part of the patient, such as the patient's wrist, arm, leg, etc. For example, retainer 250 may include a glove positionable over the patient's hand and/or wrist, or a sock providing pedal access positionable around the patient's foot and/or ankle. In various exemplary embodiments, retainer 250 may include one or more of an adhesive tape, clip, snap, elastic sleeve or band, for example. Retainer 250 may include one or more retention features (FIG. 4) that releasably retain tube 110 in a fixed position relative to access point 30 (e.g. to provide an anchoring effect and/or reduce the likelihood of unintended withdrawal of catheter 20 or sheath assembly 100). In an exemplary embodiment, retainer 250 is arranged entirely outside of the patient's body (e.g. retainer 250 does not include suture attachment wings).

Catheter 20 may be an access sheath, vascular sheath, endovascular medical device, or the like, and is configured to extend through a perforation in patient 2 at access point 30 and into an anatomical conduit, such as a blood vessel. In an exemplary embodiment, catheter 20 has a proximal end 21, a distal end 24, and at least one lumen 23 extending between the proximal and distal ends 21, 22. The lumen 23 defines a pathway for delivery or withdrawal of fluids, instruments such as guide wires or other interventional tools, or a combination thereof. Catheter 20 includes a sealable connector having a septum 22 external to a patient's skin 60 that is configured to releasably mate with first end 111 of sheath assembly 100 and receive an interventional tool. One or more lumens 23 may extend just under the skin, and have a length between 2 cm and 10 cm, for example, or may extend a greater distance into a patient, and have a length between 10 cm and 100 cm or more, for example. In some embodiments, catheter 20 may be a bifurcated catheter, or a peel-away catheter, including two or more lumens and two or more sealable connectors each having a septum (e.g. catheter may include two or more hemostasis valves). In some embodiments, catheter 20 includes one or more side arms 25. Side arm 25 defines a central lumen and may include one or more valve devices or other components. Side arm 25 may be used to aspirate air and blood and facilitate improved suction and/or aspiration of the thrombus/clot. In an exemplary embodiment, side arm 25 may flex and bend without kinking or substantially blocking the central lumen, and for example may bend at least between a substantially straight configuration and a configuration that forms a 180° curve, 90° curve, or 45° curve.

Medical sheath system 10 facilitates effective operation by practitioner 1 on patient 2 from an ergonomic position and/or outside of the strongest locations of radiation field 14 in a medical environment. In use, catheter 20 is positioned through access point 30 along an insertion axis (A). Insertion axis (A) extends in a direction along lumen 23 at a location passing through access point 30. A medical device 40 (e.g. including an extension sheath and/or interventional tool) may be manipulated by practitioner 1 to advance the interventional tool through access point 30 along insertion axis (A). Support sheath 100 is positioned between catheter 20 and medical device 40 and provides support and stability against forces exerted by an interventional tool advanced during operation.

Support sheath 100 may have a curved configuration such that the distal portion 100a of tube 110 has an orientation different than proximal end 100b when attached to catheter 20. For example, distal portion 100a may be fixed in a predetermined orientation relative to proximal end 100b when attached to catheter 20. In some embodiments, tube 110 has a curved configuration forming a 90° curve between first and second ends 111, 112. Distal portion 100a may be parallel to insertion axis (A) (e.g. substantially parallel, within 15° of exactly parallel) and proximal portion 100b may be perpendicular to insertion axis (A) (e.g. substantially parallel, within 15° of exactly parallel). Accordingly, tube 110 may be configured to receive an interventional tool through second end 112 in a orientation that is angled relative to insertion axis (A). Medical device 40 may thus at least partially have an orientation that is angled relative to insertion axis (A). In some embodiments, at least a portion of medical device 40 may be oriented perpendicular to insertion axis (A) during advancement of the interventional tool through tube 110, catheter 20, and access point 30.

Support sheath 100 may have a particular curvature to orient proximal end 100b at a selected angle relative to distal end 100a. In various exemplary embodiments, tube 110 may have a curved configuration forming a curve between 0° and 180°, 45° and 135°, or 60° and 120°. For example, tube 110 may have a curved configuration forming a curve of 0° (e.g. such that the support sheath is straight), 30°, 45°, 60°, 75°, 90°, 105°, 120°, 135°, 150°, or 180°. Such configurations may provide a selected angle for a particular procedure, or provide an angle preferred by a particular practitioner to facilitate ergonomic advancement and easy manipulation of an interventional tool, while providing adequate support and stability.

Configurations in which practitioner 1 advances an interventional device in a direction angled relative to insertion axis (A) may facilitate ergonomic operation and reduced orthopedic stress of practitioner 1. For example, practitioner 1 may effectively manipulate medical device 40 to advance the interventional tool while standing in an upright posture. An upright posture may reduce stress and fatigue on practitioner 1, particularly throughout an operation having an extended duration. Alternatively or additionally, support sheath 100 facilitates an orientation of medical device 40 across the body of practitioner 1 such that practitioner 1 may more comfortably manipulate medical device 40 in a natural, ergonomic position. In some embodiments, medical device 40 is positioned parallel to the shoulders of practitioner 1 between left and right hands of practitioner 1 (e.g. such that medical device 40 is about the same distance from practitioner 1 at locations handled by their left and right hands). The operator's hands may be positioned outside of field of radiation 14 during the operation, and the physician's head, neck and other body part's may be positioned a greater distance from field of radiation 14.

In an exemplary embodiment, support sheath 100 facilitates operation from a position in which the patient (e.g. access point, head, and/or chest, etc.) and a viewable display of monitor 60 are within a common field of view of practitioner 1. Practitioner 1 may thus manipulate medical device 40 (e.g. primarily using a dominant hand) while comfortably viewing patient 2 and monitor 60. For example, monitor 60 may display an image of an interventional tool within an anatomical structure, or other information relevant to practitioner 1's manipulation of medical device 40. Because support sheath 100 orients medical device 40 in a predetermined angle relative to insertion axis (A), practitioner 1 may face towards monitor 60 while medical device 40 is manipulated in front of the practitioner's body. In an exemplary embodiment, practitioner 1 may thus view monitor 60 and manipulate medical device 40 without rotating their neck, hunching their back, or otherwise straining from a natural, ergonomic position.

In the embodiment shown in FIGS. 1-3, insertion axis (A) is oriented in a direction towards monitor 60 (e.g. and extends in a direction substantially between practitioner 1 and monitor 60). Support sheath 100 may be oriented partially in a direction extending towards monitor 60 (e.g. a direction parallel to insertion axis (A)) and partially in a direction parallel to the viewable display of monitor 60 (e.g. a direction perpendicular to practitioner 1's view of monitor 60). For example, proximal portion 100b of tube 110 may extend in a direction parallel to monitor 60 and/or extend in a direction parallel to practitioner 1's body (e.g. a direction across the shoulders of practitioner 1). Alternatively or additionally, medical device 40 may extend in a direction parallel to monitor 60 and/or in a direction parallel to practitioner 1's body (e.g. a direction across the shoulders of practitioner 1). Such configurations may facilitate a practitioner posture during operation in which practitioner 1 faces towards monitor 60 with shoulders square to monitor 60. Left and right hands are equidistant (e.g. substantially equidistant, within 15%) from medical device 40, such that practitioner 1 can manipulate medical device 40 in front of their body with their hands in natural, ergonomic positions.

Various embodiments described herein may facilitate advantageous positioning of an operating side table 70. For example, side table 70 may be positionable in front of practitioner 1 such that practitioner 1 faces side table 70. Side table 70 may support medical device 40, including an interventional tool and/or other components used during an operation. In some embodiments, side table 70 is positioned between practitioner 1 and monitor 60 during advancement of the interventional tool through access point 30.

In an exemplary embodiment, support sheath 100 facilitates manipulation of medical device 40 using a selected hand, such as a right hand for right-hand dominant practitioners and a left hand for left hand dominant practitioners. A curved configuration of support sheath 100 may allow practitioner 1 to stand perpendicular to patient 2, (e.g. such that practitioner 1 faces in a direction along a height of the patient), and a dominant hand to be spaced away from the patient. In the example shown in FIGS. 1-3, the practitioner's left hand is positioned closest to patient 2 (e.g. and closest to access location 30) and may be used primarily to support and stabilize medical device 40, while the practitioner's right hand is positioned relatively further from patient 2 and may be the dominant hand used primarily to manipulate, control, and advance the medical device, such as an interventional tool.

Support sheath 100 may provide flexibility in selecting the location of access point 30 on the body of patient 2, while simultaneously allowing practitioner 1 to operate from a selected posture and position. For example, in various medical operations, multiple possible access points may be available to provide suitable access to a treatment area through which an interventional tool may be delivered. In some scenarios, different access points may offer a different set of advantages and difficulties, while also affecting the posture and position that a practitioner 1 must operate from. Percutaneous coronary intervention (PCI) operations, for example, are commonly performed by accessing the left or right common femoral artery (e.g. proximate a groin location), or the left or right radial artery (e.g. proximate a wrist location). In conventional treatment procedures, a practitioner often selects an access point 30 for access to the right radial artery or the right common femoral artery in order to facilitate right-handed manipulation of an interventional tool, with less consideration given to advantages in patient treatment that may result from operating on the left radial artery or left common femoral artery (e.g. such as a shorter distance to a treatment location or less interaction with intermediate anatomical structures). In some exemplary embodiments, support sheath 100 facilitates operation by a dominant hand irrespective of which side of the patient a practitioner operates from. Accordingly, a practitioner may select an access point 30 based on patient outcome advantages, and in some embodiments, while being less limited by ergonomic considerations. Access point 30 may thus be located on a left fore arm or wrist to access the left radial artery in a percutaneous coronary intervention (PCI) procedure, while practitioner 1 may control and manipulate the interventional tool primarily using their right hand. Alternatively or additionally, a practitioner may orient a patient's arm or leg (e.g. where access point 30 is located) in a desired orientation while support sheath 100 may be orient medical device 40 in an ergonomic position away from radiation field 14. In various exemplary embodiments, patient 2's arm, for example, may be positioned along patient 2's body or may be extending outwards, while an curve of support sheath 100 selected to provide ergonomic or operational advantages.

Support sheath 100 may be used in any suitable procedure, and may be particularly advantageous in image guided surgery procedures in which access site restraints may inhibit workflow or physician ergonomics and/or expose an operator to radiation. In an exemplary embodiment, sheath assembly 100 may be used in one or more of percutaneous coronary intervention (PCI) from the right or left radial artery or right or left common femoral artery, carotid artery and subclavian artery intervention for acute strokes, vascular malformations, and aneurysms, central vein access for electrophysiology procedures, hemodialysis intervention, arteriovenous fistula (AVF) intervention, antegrade percutaneous arterial intervention of the femoral artery or other vessel, obese patient access, contralateral groin access, electrophysiological cardiology procedures, pacemaker insertions, renal collecting system intervention, ureteral strictures, urinary conduit formation, treatment of the biliary tree, portal venous system, gastrointestinal tract or spinal canal, trans sternum positioning and/or other suitable applications. In various exemplary embodiments, sheath assembly 100 allows a physician or healthcare practitioner to operate near an extremity and away from a patient's abdomen, chest and head, while using a preferred hand for primary manipulation and control. Similarly, a physician or healthcare practitioner may operate distant from a maximum radiation field that may be directed proximate a patient access site and/or treatment location.

In various exemplary embodiments, support sheath 100 provides a modular system that may be used with one or more additional components to provide additional functionality and/or flexibility. For example, tube 110 may be joined, directly or indirectly, with exhalable or detachable appendages. A curved portion that is larger or having a greater length may be used for larger patients receiving lower extremity intervention, for example. A Toughy-Borst fitting may be used to facilitate simultaneous introduction of a fluid while using a guide wire during catheterization. A double lumen or bifurcated sheath may be used for therapy requiring two wires and access sites. A larger internal diameter may be used to create relatively larger communication for a suction thrombectomy, for example.

A support sheath may be provided as a kit including one or more inflexible tubes, curvable tubes, adapters, and/or retainer devices. An exemplary embodiment of a kit includes first and second inflexible tubes having different curved configurations with different fixed angles. Alternatively or additionally, the inflexible tubes may have different lengths and/or diameters, such that a practitioner my select a desired support sheath at a time of use as desired for a particular patient or treatment. For example, a longer tube may be used to facilitate antegrade access to the femoral artery for peripheral vascular disease treatment of the ipsilateral extremity, and allow the physician or healthcare practitioner to operate proximate a patient's legs rather than a patient's abdomen, for example. Similarly, an exemplary embodiment of a kit may include first and second curvable tubes having the same or different lengths and/or diameters, such that a physician or healthcare practitioner may customize a sheath assembly at a time of use as desired for a particular patient or treatment. In some embodiments, the kit further includes a retainer configured to secure the support sheath to a surface, and/or retain the tube in a particular curved configuration.

In some exemplary embodiments, two or more tubes may be connected in series to provide a desired length and path for a particular patient or treatment. For example, a first end of a first tube may be connected to a second end of a second tube to increase a length of the sheath assembly, and/or travel along a desired path relative to anatomical features of the patient. A length of the support sheath may thus be customized by a physician or healthcare practitioner at a point of use.

Figure 4:
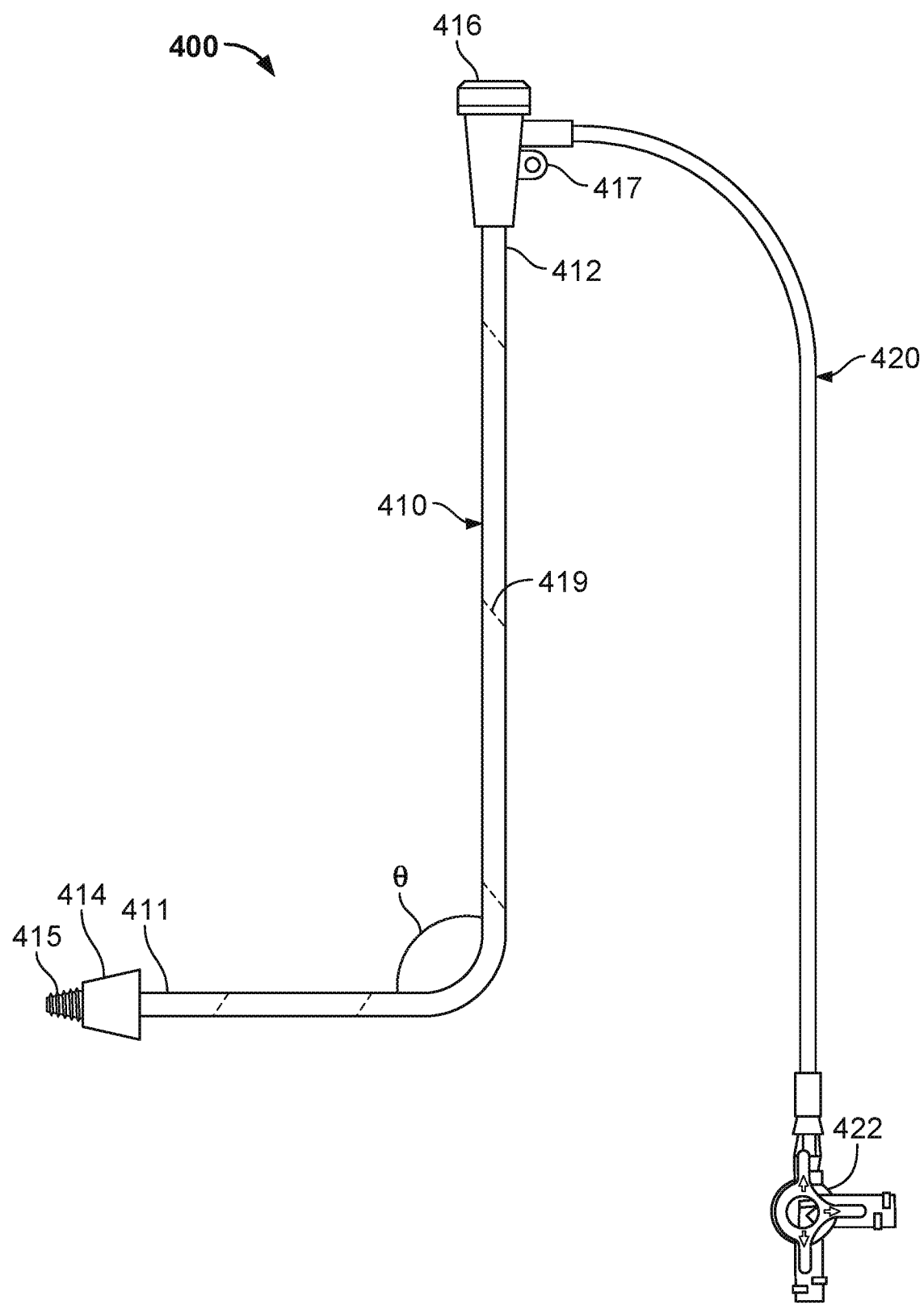
FIG. 4 is a plan view of an exemplary support sheath having a curved configuration.
Figure 5:
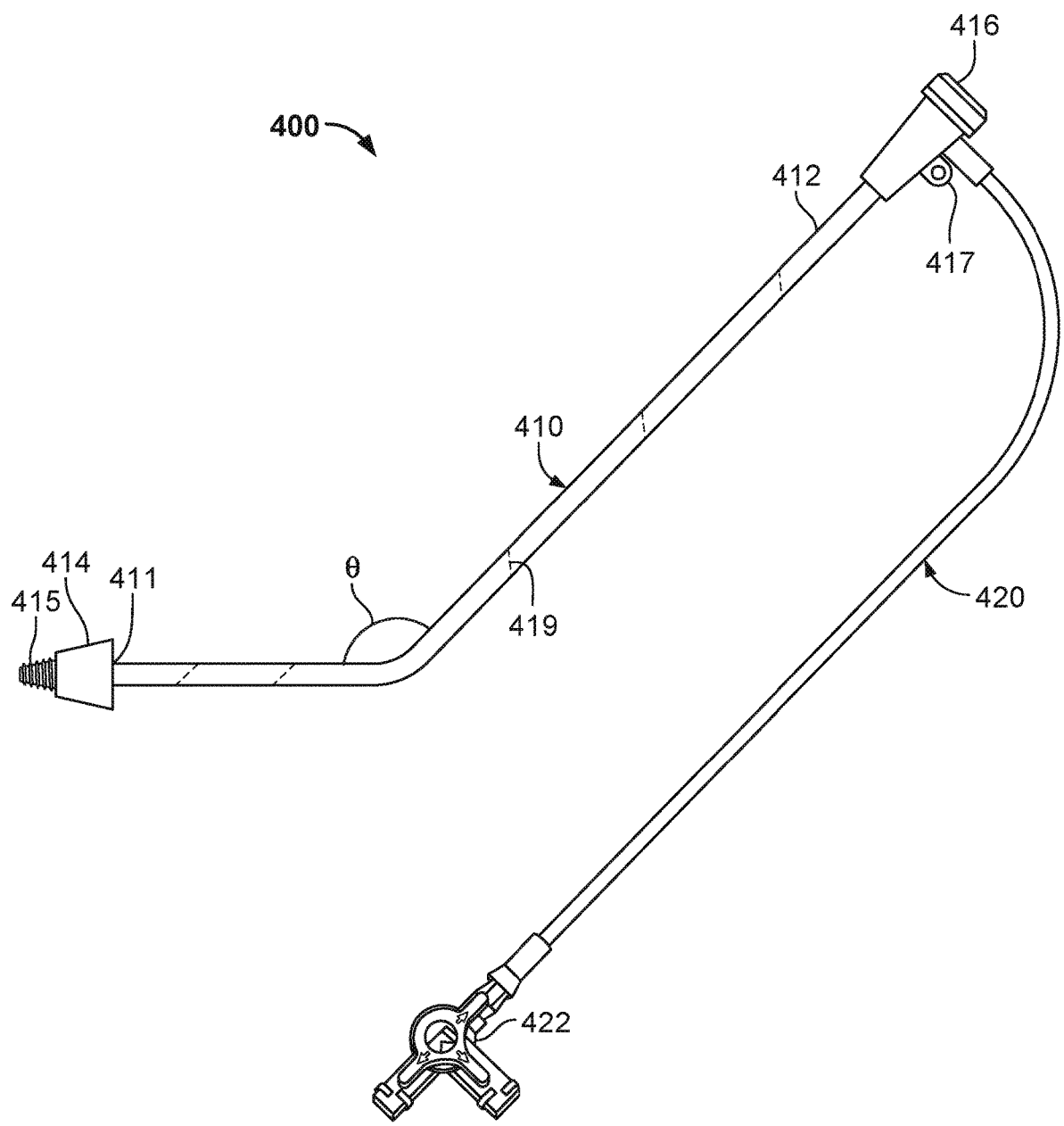
FIG. 5 is a plan view of an exemplary support sheath having a curved configuration.

Referring now to FIGS. 4 and 5, an exemplary support sheath 400 is shown. In various exemplary embodiments, support sheath 400 may have features similar to, and be suitable for similar applications as, support sheath 100 described above with reference to FIGS. 1-3. Support sheath 400 includes a tube 410 and a side arm 420. In an exemplary embodiment, tube 410 provides access to a catheter, for example, such as an introducer sheath or other vascular access component, and provides a support sheath extension that may be used at a vascular access site.

Tube 410 includes a first end 411, second end 412 and an elongate portion 413. Elongate portion 413 defines a central passage or lumen through which an interventional tool, medicine, or other suitable component may be delivered to or extracted from a vascular access site. First end 411 may include a connector end configured to be joined with a hemostasis valve or other port or connector of a catheter 20 (FIGS. 1-3), such as an introducer sheath or other intravenous access component. Second end 412 may include a port 416 providing an opening for an interventional tool, medicine or other suitable component to be passed through tube 410 and into a patient access site.

In an exemplary embodiment, first end 411 of support sheath 410 includes a connector, such as an adapter 414. Adapter 414 may be removably or permanently joined to first end 411 and includes one or more attachment features 415 configured to couple with catheter 20, for example.

Adapter 414 may be removably or permanently attachable to allow communication between tube 410 and catheter 20. In an exemplary embodiment, attachment features include helical threads compatible with one or more introducer sheaths, such as AVANTI+ introducer sheath available from Cordis, the BRITE TIP interventional sheath available from Cordis, the GLIDESHEATH introducer sheath available from Terumo Medical Corporation, SUPER SHEATH introducer sheath available from Boston Scientific Corporation, INPUT introducer sheath available from Medtronic, other introducer sheaths, or components providing vascular access to a patient for the introduction of an interventional tool, medicine, or other component. In various exemplary embodiments, attachment features may include a luer lock connector, bayonet connector, snap connector, or other attachment feature to allow secure connection between adapter 414 and the catheter. In some exemplary embodiments, adapter 414 is configured for attachment to a second end 412 of support sheath 100, such that two or more support sheaths may be connected in series. In an exemplary embodiment, adapter 414 has a widened body to facilitate handling (e.g. a body thicker than tube 410). In some embodiments, the widened body may have a curved surface or one or more features such as texture, ribs, etc. to facilitate handling.

Second end 412 of tube 410 includes a port 416, such as a septum hub port. Port 416 includes at least a first opening for insertion of an interventional tool that may be passed through tube 410, through a component attached at first end 411, and/or into a patient access location, and may include a hemostasis valve. In some exemplary embodiments, port 416 includes a suture connector 417 defining an opening that one or more sutures may be passed through to secure port 416 and second end 412 of tube 410 in a desired location.

In an exemplary embodiment, port 416 defines a septum hub that a side arm 420 may be attached to. Side arm 420 defines a central lumen and may include one or more valve devices or other components, such as a three-way stop cock 422. Side arm 420 may be used to aspirate air and blood and allow for improved suction and/or aspiration of the thrombus/clot. In an exemplary embodiment, side arm 420 may flex and bend without kinking or substantially blocking the central lumen, and for example may bend at least between a substantially straight configuration and a configuration forming a 180° curve, 90° curve or 45° curve.

In an exemplary embodiment, three-way stop cock 422 may allow infusion of contrast, saline solution, or other component, aspiration, collection of blood or other sample, or passage to tube 410 and an access point of a patient. In some exemplary embodiments, three-way stop cock 422, side arm 420 and/or other suitable components of support sheath 400 are suitable for high pressure applications. For example, three-way stop cock 422, side arm 420 and/or other suitable components may be suitable for applications requiring pressures between 400 psi and 1000 psi, 600 psi and 900 psi, 700 psi and 850 psi, or about 800 psi.

In an exemplary embodiment, tube 410 is made at least in part from a medical grade polymer including a polyether block amide (PEBA), such as PEBAX 55D available from Arkema Inc., or other suitable material. In some exemplary embodiments, curvable tube 410 may include one or more additional materials lining a central lumen to provide one or more of hydrophilicity, hydrophobicity, low friction, or other suitable property. For example, curvable tube 410 may include an interior surface including a polytetrafluoroethylene (PTFE), such as TEFLON available from E.I DuPont de Nemours & CO.

Tube 410 of support sheath 400 may be an inflexible tube that permanently retains a fixed curved configuration. In an exemplary embodiment, tube 410 includes a rigid tube that is not readily bent and/or repeatedly returns to its original curved configuration. Inflexible tube may be made from a rigid polymer material, such as molded, extruded, etc. from a rigid polymer material. Alternatively or additionally, tube 410 may include one or more structures or layers that retain tube 410 in a curved configuration having a fixed angle. For example, tube 410 may include a coiled wire 419, overmolded rigid support structures, or other components that impart tube 410 with a fixed angle. Support sheaths 400 having a fixed angle may provide simplified operation in the medical environment by reducing manipulation required by a practitioner to configure support sheath 400 in a selected configuration. In some embodiments, multiple support sheaths 400 may be provided as a kit so that a practitioner may simply select a particular configuration (e.g. instead of bending a tube into a desired configuration in the medical environment). In various exemplary embodiments, support sheath 400 may include an inflexible tube 410 curved with a fixed angle ($\Theta$) of 90° (FIG. 4), an inflexible tube 410 curved with a fixed angle ($\Theta$) of 135° (FIG. 5), or an inflexible tube 410 having another fixed angle.

In some exemplary embodiments, tube 410 may be a curvable tube configured to bend between a substantially straight configuration in which first end 411 is linearly distal to second end 412, and one or more curved configurations in which first end 411 is not linearly distal to second end 412. For example, curvable tube 410 may be bent into a selected configuration by a practitioner in the medical environment at a time of use of tube 410, such as a configuration in which tube 410 has a 90° curve (FIG. 4), 135° curve (FIG. 5), or other selected configuration. In embodiments in which tube 410 is a curvable by a practitioner in the medical environment, tube 410 may be curved or bent without substantially kinking or otherwise blocking a central lumen or channel defined by tube 410.

Tube 410 may include one or more additional elements to prevent kinking and/or to allow tube 410 to at least partially retain a curved configuration without a separate retainer device (e.g. particularly in exemplary embodiments in which tube 410 is a curvable tube). In an exemplary embodiment, tube 410 includes a coiled wire 419 in a polymer material of a wall. For example, a nitinol, stainless steel, or other suitable coil may be impregnated in curvable tube 410 such that curvable tube 410 is flexible and kink-resistant. In some embodiments, a metallic coil may allow curvable tube 410 to retain a curved configuration when bent or flexed.

Figure 6:
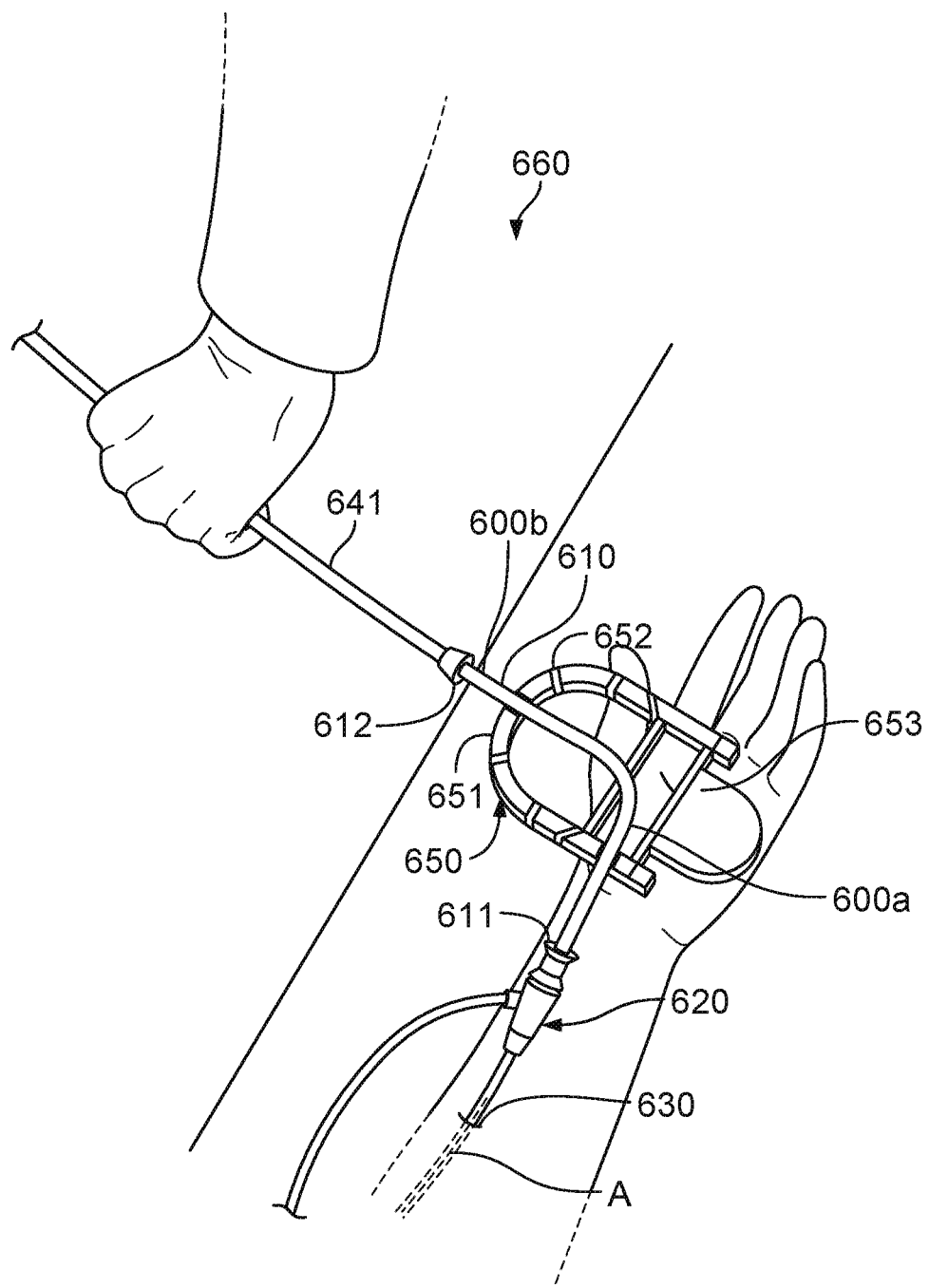
FIG. 6 is a perspective view of an exemplary medical sheath system including a retainer.

Referring to FIG. 6, an exemplary medical sheath system 660 is shown, including exemplary support sheath 600. In various exemplary embodiments, medical sheath system 660 and support sheath 600 may have features similar to medical sheath system 10 and support sheaths 100 or 400, described herein.

Support sheath 600 includes a tube 610 having a curved configuration such that the distal portion 600a of tube 610 has an orientation different than proximal end 600b when attached to catheter 620. For example, distal portion 600a is fixed in a predetermined orientation relative to proximal end 600b when attached to catheter 620. In some embodiments, tube 610 has a curved configuration including a 90° curve between first and second ends 611, 612. Distal portion 600a may be parallel to insertion axis (A) and proximal portion 600b may be perpendicular to insertion axis (A). Accordingly, tube 610 is configured to receive an interventional tool 641 through second end 612 in an orientation that is angled relative to insertion axis (A). Interventional tool 641 may thus at least partially have an orientation that is angled relative to insertion axis (A). For example, at least a portion of interventional tool 641 may be oriented perpendicular to insertion axis (A) during advancement of the interventional tool through tube 610, catheter 620, and access point 630.

In an exemplary embodiment, medical sheath system 660 includes a retainer 650 configured to secure support sheath 600 to a surface and/or retain tube 610 in a desired configuration. Retainer 650 includes a plurality of retention features 651 that may selectively engage one or more portions of tube 610. In an exemplary embodiment, retainer 650 may retain tube 610 in a first configuration in which tube 610 forms a 90° curve, or may retain tube 610 in one or more additional configurations to accommodate a curved configuration of tube 610 as selected for a particular application or treatment location, or to allow a physician or healthcare practitioner to more easily work outside of a radiation field, for example.

In an exemplary embodiment, retainer device 650 includes a frame 651 and one or more retention features 652 configured to hold a curvable portion and/or other components of an exemplary sheath assembly in a selected configuration. Retainer device 650 may be positioned proximate a patient access site, for example, to facilitate handling and use of a sheath assembly. For example, when used to access a radial artery, retainer 650 may be positioned on a hand, wrist, or other location of a patient's arm to secure support sheath 600 in a desired position relative to access point 630.

Retention features 652 may include a feature configured to retain support sheath in a desired position. In an exemplary embodiment, retention features 652 include one or more channels sized to receive at least a portion of a support sheath 610. For example, retainer device 650 includes a plurality of channels that at least a portion of support sheath 610 may be selectively engaged within. The plurality of channels provide a number of suitable orientations and configurations such that a sheath assembly may be retained having any of multiple curved configurations that range, for example, in increments between 0° to 180°. In various exemplary embodiments, retainer device 650 may include channels spaced and/or oriented in 15°, 30°, 45°, 60°, 90°, or other suitable increments to allow an operator to select a desired configuration.

Retainer device 650 may have any suitable configuration to retain all or a portion of a support sheath 600 in a desired configuration. For example, frame 651 of retainer device 650 may define channels 652 spaced along a perimeter of frame 651. In an exemplary embodiment, frame 651 has a substantially U-shaped configuration. Channels 652 are spaced about the perimeter of frame 651, and one or more channels define channel axes that are orthogonal to the U-shaped frame.

In an exemplary embodiment, retainer 650 includes a base 653. In the embodiment shown in FIG. 6, base 653 includes a substantially planar lower surface that provides stability when retainer device 650 is supported by or attached to a surface. For example, lower surface may include an adhesive and a removable liner. The liner may be removed at a time of use to expose the adhesive of lower surface such that lower surface and retainer device 650 may be adhered to a patient's body, for example proximate an access site, a covering, or other suitable surface where a sheath assembly may be retained. In some example embodiments, lower surface 654 may include a medical grade foam adhesive tape, or other suitable component to adhere retainer device 650 to an appropriate surface. Alternatively or additionally, base 653 may include a clip, such as a spring-loaded clip, textured or non-slip lower surface, or may include a soft or rubberized material. An adhesive or non-slip lower surface maintains retainer device 250 in a desired position and may minimize tension or stress that could otherwise result at a patient access point when a needle, guidewire, or other component, for example, is advanced through tube 610. Retainer device 650 may thus serve as an anchor to maintain a catheter and/or sheath assembly in a stable position relative to a patient access opening.

Frame 651 may be made from any suitable material such that one or more components of a sheath assembly may be retained by retainer device 650. In an exemplary embodiment, frame 651 is integrally formed from a plastic, such as a polyamide. Such a material may provide sufficient stiffness and stability. In some embodiments, retainer device 650 is formed of a material that may not readily be plastically deformed and/or that maintains respective channels 652 fixedly positioned relative to one another. In other exemplary embodiments, retainer device 650 may be bendable or shapeable such that frame 651 may be shaped as desired by a physician or healthcare practitioner at a time of use, and will retain its shape when a portion of a sheath assembly is engaged with retainer device 650.

In some exemplary embodiments, frame 651 may be made of a radio-transparent material that does not block or substantially interfere with imaging equipment. A radio-transparent material may thus allow retainer device 650 to be positioned as desired based on operational or ergonomic factors, rather than positioning as may otherwise be necessary to avoid imaging interference.

Figure 7:
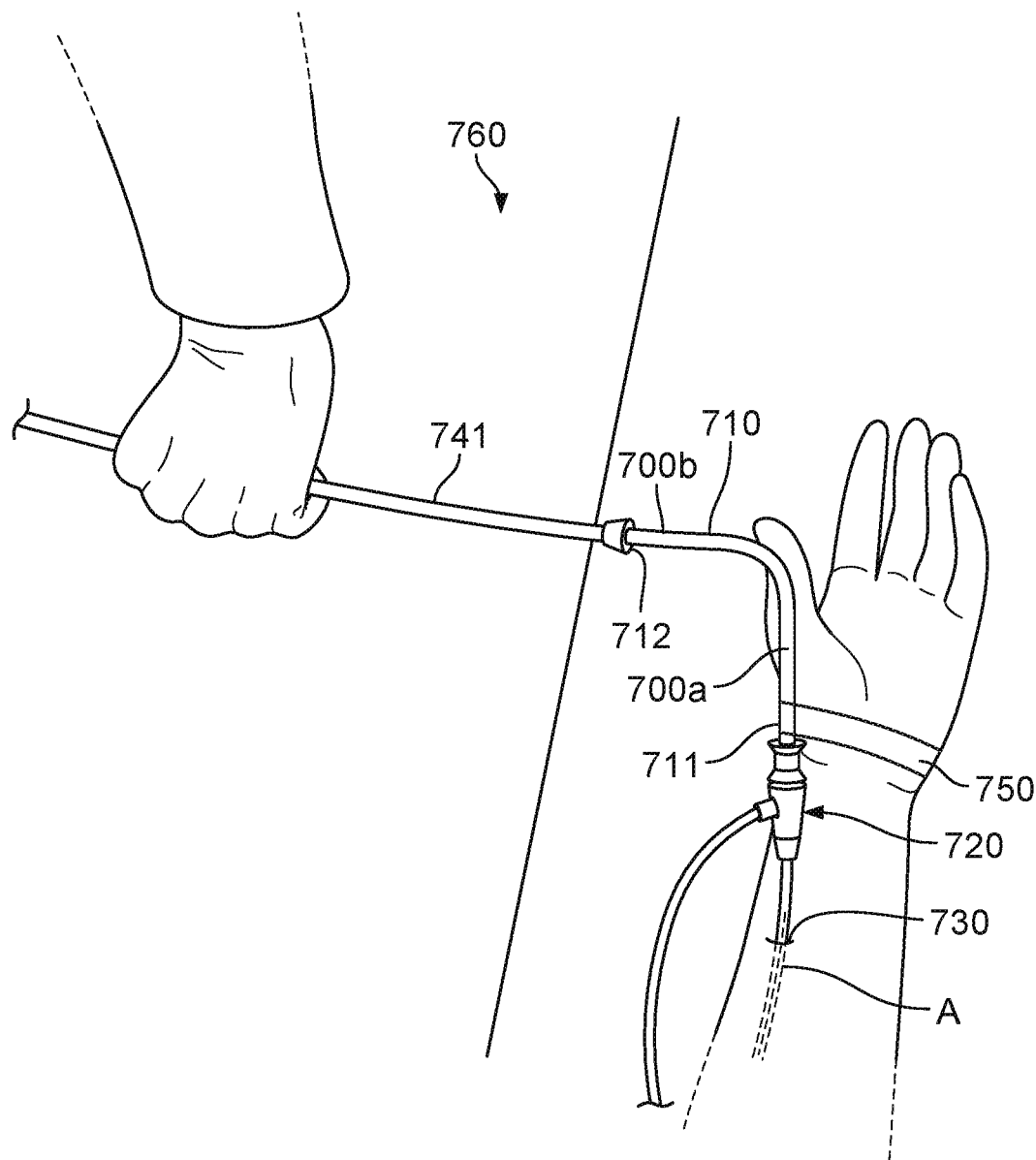
FIG. 7 is a perspective view of an exemplary medical sheath system including a retainer.

Referring to FIG. 7, an exemplary medical sheath system 760 is shown, including exemplary support sheath 700. In various exemplary embodiments, medical sheath system 760 and support sheath 700 may have features similar to medical sheath system 10 and 660, and support sheaths 100, 400, or 600, described herein.

Support sheath 700 includes a tube 710 having a curved configuration such that the distal portion 700a of tube 710 has an orientation different than proximal end 700b when attached to catheter 720. For example, distal portion 700a is fixed in a predetermined orientation relative to proximal end 700b when attached to catheter 720. In some embodiments, tube 710 has a curved configuration forming a 90° curve between first and second ends 711, 712. Distal portion 700a may be parallel to insertion axis (A) and proximal portion 700b may be perpendicular to insertion axis (A). Accordingly, tube 710 is configured to receive an interventional tool 741 through second end 712 in an orientation that is angled relative to insertion axis (A). Interventional tool 741 may thus at least partially have an orientation that is angled relative to insertion axis (A). For example, at least a portion of medical device 741 may be oriented perpendicular to insertion axis (A) during advancement of the interventional tool through tube 710, catheter 720, and access point 730.

In an exemplary embodiment, medical sheath system 760 includes a retainer 750 configured to secure support sheath 700 to a surface and/or retain tube 710 in a desired configuration. Retainer 750 may be a sleeve, such as an elastic sleeve, tape, adhesive pad, or the like. In an exemplary embodiment, retainer 750 extends around a portion of a patient's body to secure support sheath 700 in a fixed positioned relative to access point 730. For example, retainer 750 may surround a hand, wrist, fore arm, leg, or other anatomical feature of the patient's body. In other exemplary embodiments, retainer 750 does not extend entirely around an anatomical feature of the patient's body, and an adhesive pad, for example, may secure support sheath 710 to the patient's skin or another surface.

Figure 8:
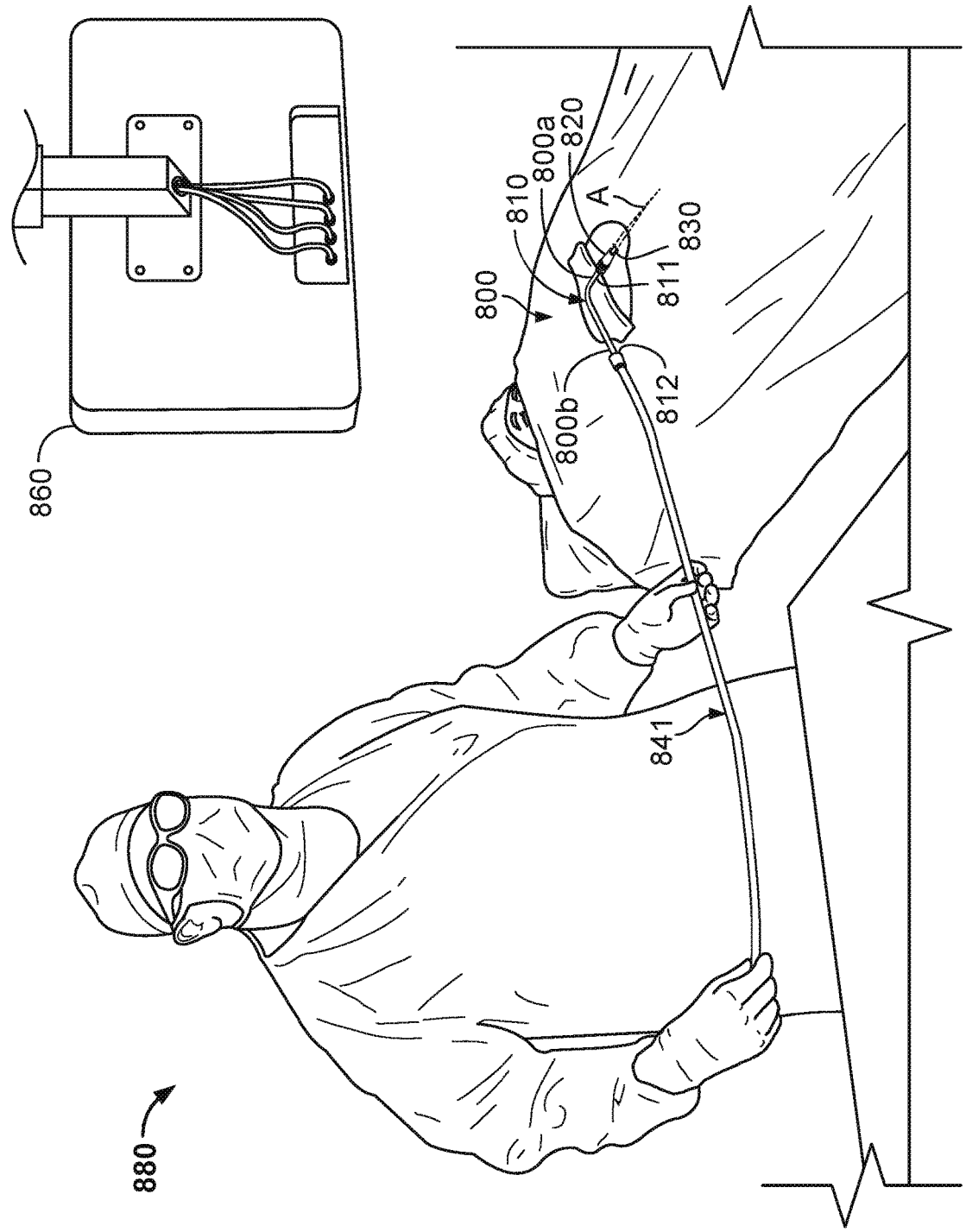
FIG. 8 is perspective view of an exemplary medical sheath system in use in a medical environment.

Referring to FIG. 8, an exemplary medical sheath system 860 is shown, including exemplary support sheath 800. In various exemplary embodiments, medical sheath system 860 and support sheath 800 may have features similar to medical sheath system 10, 660 and support sheaths 100, 400, 600 described herein. In the embodiment shown in FIG. 8, access point 830 is positioned proximate a groin region of a patient for common femoral artery access. Medical sheath system 860 facilitates a selected position and posture for practitioner 1 during operation.

Support sheath 800 includes a tube 810 having a curved configuration such that the distal portion 800*a* of tube 810 has an orientation different than proximal end 800*b* when attached to catheter 820. For example, distal portion 800*a* is fixed in a predetermined orientation relative to proximal end 800*b* when attached to catheter 820. In some embodiments, tube 810 has a curved configuration including a 90° curve between first and second ends 811, 812. Distal portion 800*a* may be parallel to insertion axis (A) and proximal portion 800*b* may be perpendicular to insertion axis (A). Accordingly, tube 810 is configured to receive an interventional tool 841 through second end 812 in an orientation that is angled relative to insertion axis (A). Interventional tool 841 may thus at least partially have an orientation that is angled relative to insertion axis (A). For example, at least a portion of interventional tool 841 may be oriented perpendicular to insertion axis (A) during advancement of the interventional tool through tube 810, catheter 820, and access point 830.

Configurations in which practitioner 1 advances an interventional device in a direction angled relative to insertion axis (A) may facilitate ergonomic operation and reduced orthopedic stress of practitioner 1, such as a procedure involving common femoral artery access. For example, practitioner 1 may effectively advance interventional tool 841 while standing in an upright posture. An upright posture may reduce stress and fatigue on practitioner 1, particularly throughout an operation having an extended duration. Alternatively or additionally, support sheath 800 facilitates an orientation of interventional tool 841 across the body of practitioner 1 such that practitioner 1 may more comfortably manipulate interventional tool 841 in a natural, ergonomic position. In some embodiments, interventional tool 841 is positioned parallel to the shoulders of practitioner 1 between left and right hands of practitioner 1 (e.g. such that interventional tool 841 is about the same distance from practitioner 1 at locations handled by their left and right hands). The operator's hands may be positioned outside of field of radiation during the operation, and the physician's head, neck and other body part's may be positioned a greater distance from field of radiation 14. Alternatively or additionally, practitioner 1 may manipulate interventional tool 841 (e.g. primarily using a dominant hand) while comfortably viewing the patient and monitor 860. Practitioner 1 may face towards monitor 860 while interventional tool 841 is manipulated in front of the practitioner's body. In an exemplary embodiment, practitioner 1 may thus view monitor 860 and manipulate interventional tool 841 without rotating their neck, hunching their back, or otherwise straining from a natural, ergonomic position.

In the embodiment shown in FIG. 8, insertion axis (A) is oriented in a direction towards monitor 860 (e.g. and extends in a direction substantially between practitioner 1 and monitor 860). Support sheath 800 may be oriented partially in a direction extending towards monitor 860 (e.g. a direction parallel to insertion axis (A)) and partially in a direction parallel to the viewable display of monitor 860 (e.g. a direction perpendicular to practitioner 1's view of monitor 860). For example, proximal portion 800*b* of tube 810 may extend in a direction parallel to monitor 860 and/or extend in a direction parallel to practitioner 1's body (e.g. a direction across the shoulders of practitioner 1). Alternatively or additionally, interventional tool 841 may extend in a direction parallel to monitor 860 and/or in a direction parallel to practitioner 1's body (e.g. a direction across the shoulders of practitioner 1). Such configurations may facilitate a practitioner posture during operation in which practitioner 1 faces towards monitor 860 with shoulders square to monitor 860. Left and right hands are equidistant (e.g. substantially equidistant, within 15%) from interventional tool 861, such that practitioner 1 can manipulate interventional tool 861 in front of their body with their hands in natural, ergonomic positions.

Figure 9:
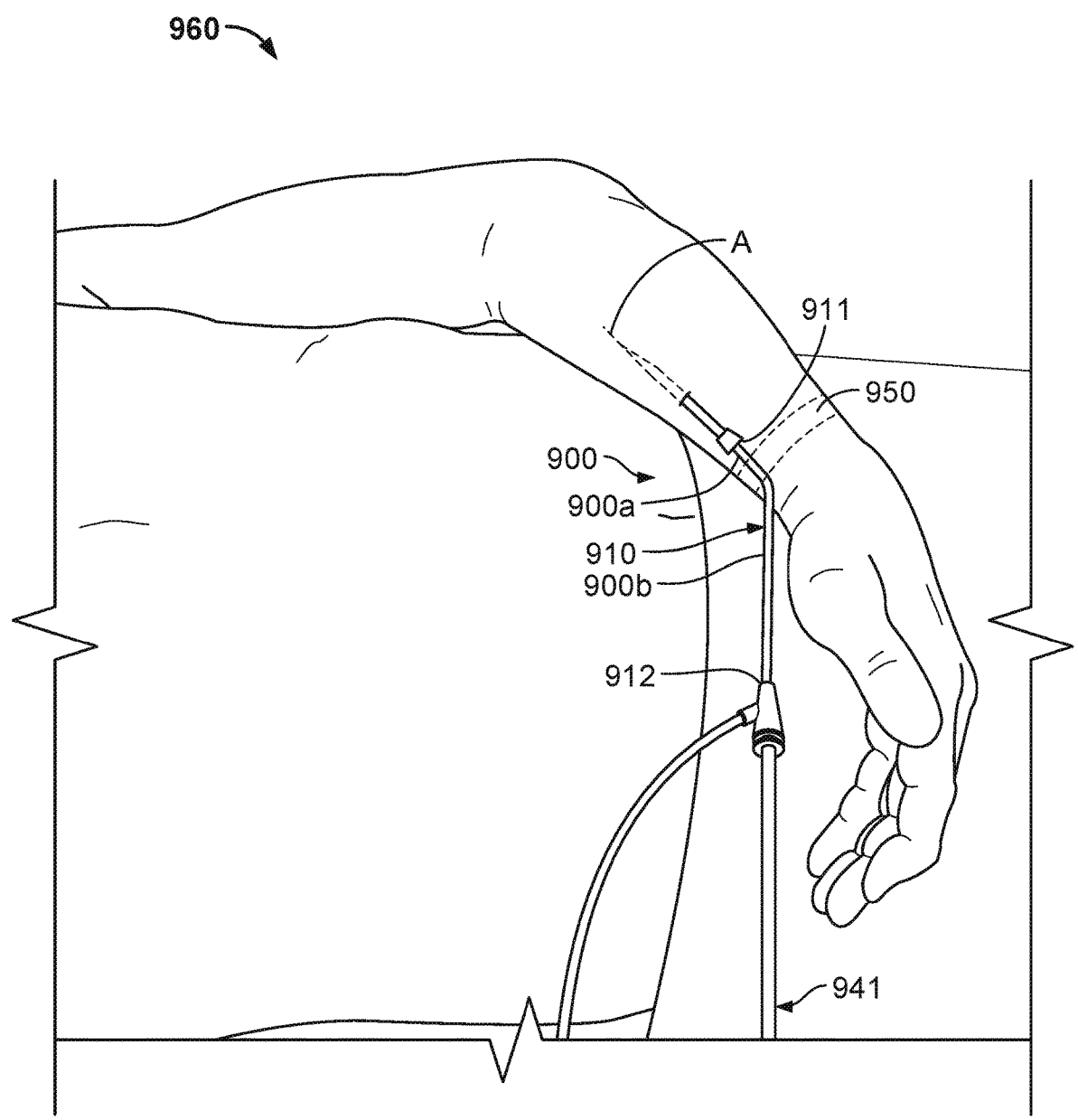
FIG. 9 is a perspective view of an exemplary medical sheath system in use in a medical environment.

Referring to FIG. 9, an exemplary medical sheath system 960 is shown, including exemplary support sheath 900. In various exemplary embodiments, medical sheath system 960 and support sheath 900 may have features similar to medical sheath system 10, 660, 860 and support sheaths 100, 400, 600, 800 described herein. In the embodiment shown in FIG. 9, access point 930 is positioned proximate a fore arm of a patient for radial artery access. The patient's arm is positioned at least partially across their body so that a practitioner may operate from the opposite side of the patient (e.g. the practitioner may operate from the right side of the patient via an access point 930 located on the left arm of the patient). Medical sheath system 960 facilitates a selected position and posture for a practitioner during operation.

Support sheath 900 includes a tube 910 having a curved configuration such that the distal portion 900*a* of tube 910 has an orientation different than proximal end 900*b* when attached to catheter 920. For example, distal portion 900*a* is fixed in a predetermined orientation relative to proximal end 900*b* when attached to catheter 920. In some embodiments, tube 910 has a curved configuration including a 90° curve between first and second ends 911, 912. Distal portion 900*a* may be parallel to insertion axis (A) and proximal portion 900*b* may be perpendicular to insertion axis (A). Accordingly, tube 910 is configured to receive an interventional tool 941 through second end 912 in an orientation that is angled relative to insertion axis (A). Interventional tool 941 may thus at least partially have an orientation that is angled relative to insertion axis (A). For example, at least a portion of interventional tool 941 may be oriented perpendicular to insertion axis (A) during advancement of the interventional tool through tube 910, catheter 920, and access point 930.

Configurations in which a practitioner advances an interventional device in a direction angled relative to insertion axis (A) may facilitate ergonomic operation and reduced orthopedic stress of the practitioner, such as a procedure involving left radial artery access with a practitioner operating from a right side of the patient, or vice versa. For example, the practitioner may effectively advance interventional tool 941 while standing in an upright posture. An upright posture may reduce stress and fatigue on the practitioner, particularly throughout an operation having an extended duration. Alternatively or additionally, support sheath 900 facilitates an orientation of interventional tool 941 across the body of the practitioner such that practitioner 1 may more comfortably manipulate interventional tool 941 in a natural, ergonomic position. In some embodiments, interventional tool 941 is positioned parallel to the shoulders of the practitioner between left and right hands of the practitioner (e.g. such that interventional tool 941 is about the same distance from the practitioner at locations handled by their left and right hands). The operator's hands may be positioned outside of field of radiation during the operation, and the physician's head, neck and other body part's may be positioned a greater distance from a field of radiation. Alternatively or additionally, the practitioner may manipulate interventional tool 941 (e.g. primarily using a dominant hand) while comfortably viewing the patient and a monitor. The practitioner may face towards the monitor while the interventional tool is manipulated in front of the practitioner's body. In an exemplary embodiment, the practitioner may thus view the monitor and manipulate interventional tool 941 without rotating their neck, hunching their back, or otherwise straining from a natural, ergonomic position.

Figure 10:
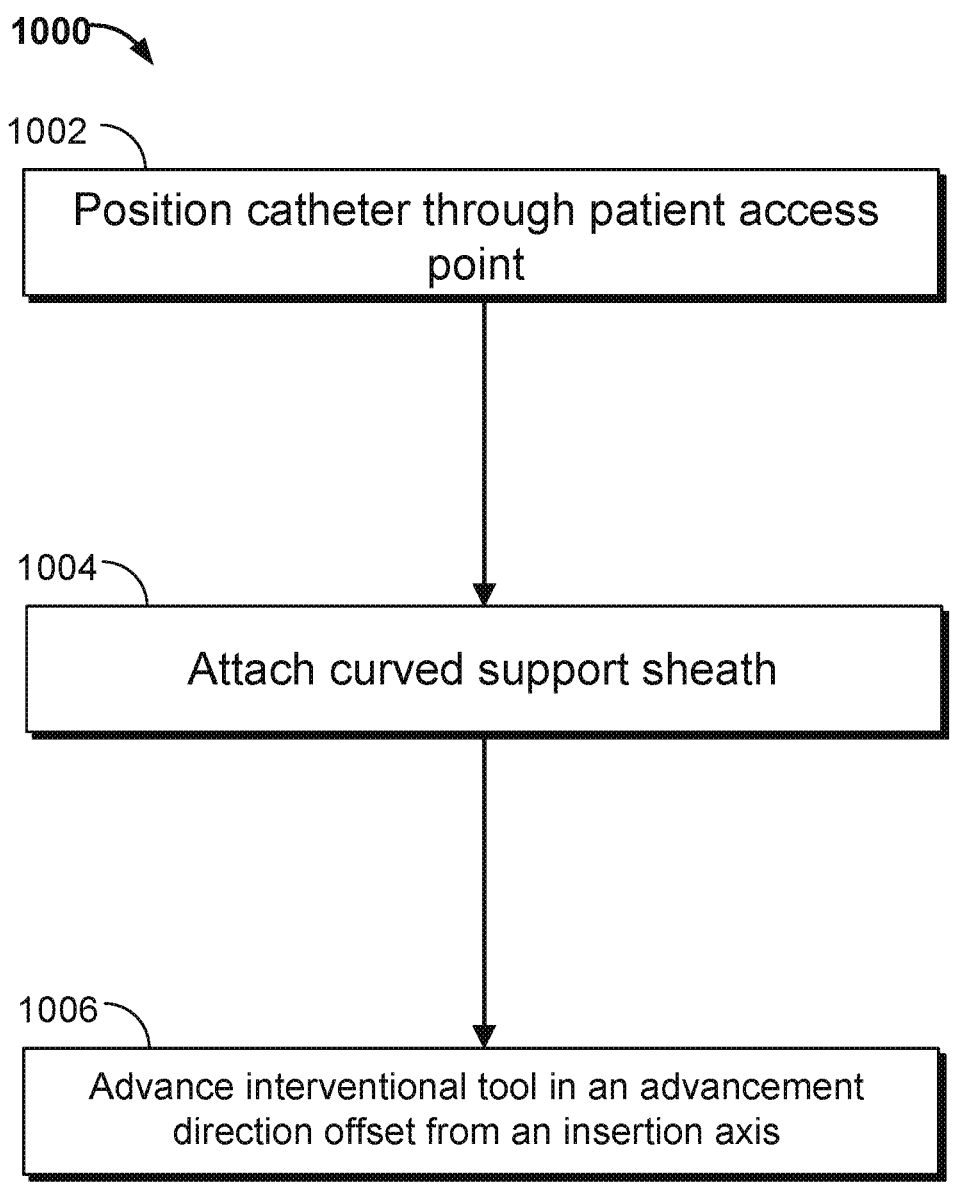
FIG. 10 is a flow diagram of an exemplary process of delivering an interventional tool.

Referring to FIG. 10, an exemplary flow diagram is shown, illustrating a method of delivering an interventional tool. Exemplary method 1000 may include operation 1002 of positioning a catheter through an access point in a side wall of an anatomical vessel of a patient in the direction of an insertion axis. A practitioner, such as a physician or healthcare practitioner, may position the catheter through the access point at the time of an operation in a medical environment.

The catheter may be an access sheath, vascular sheath, endovascular medical device, or the like, configured to extend through a perforation in a patient at the access point and into an anatomical conduit, such as a blood vessel. In an exemplary embodiment, the catheter has a proximal end, distal end, and at least one lumen extending between the proximal and distal ends. The lumen defines a pathway for delivery or withdrawal of fluids, instruments such as guide wires or other interventional tools, or a combination thereof. The catheter includes a sealable connector having a septum external to a patient's skin that is configured to releasably mate with the first end of a support sheath and receive an interventional tool.

Operation 1002 may include selecting an access point on a patient's body for a particular operation. The access point may be selected to provide access for a percutaneous coronary intervention (PCI) from the right or left radial artery or right or left common femoral artery, carotid artery and subclavian artery intervention for acute strokes, vascular malformations, and aneurysms, central vein access for electrophysiology procedures, hemodialysis intervention, arteriovenous fistula (AVF) intervention, antegrade percutaneous arterial intervention of the femoral artery or other vessel, obese patient access, contralateral groin access, electrophysiological cardiology procedures, pacemaker insertions, renal collecting system intervention, ureteral strictures, urinary conduit formation, treatment of the biliary tree, portal venous system, gastrointestinal tract or spinal canal, trans sternum positioning and/or other suitable applications.

Exemplary method 1000 may include operation 1004 of attaching a support sheath to the proximal end of the catheter. The support sheath may include a first end having a connector configured to releasably connect with the proximal end of the catheter and a second end comprising a port configured to receive an interventional tool. The support sheath may include a distal portion proximate the first end and a proximal portion proximate the second end. The distal portion may fixed in a predetermined orientation relative to the proximal end when attached to the catheter, and operation 1004 may include selecting a support sheath having a particular curve such that the distal portion is in a desired predetermined orientation relative to the proximal end. In other exemplary embodiments, the support sheath may be a curvable support sheath bendable between a straight configuration and a curved configuration. Operation 1004 may include bending the support sheath into a desired curved configuration.

Exemplary method 1000 may include operation 1006 of advancing an interventional tool by a practitioner along an advancement direction offset from the insertion axis to deliver an interventional tool within an internal access path through the tube, catheter, and anatomical vessel. The advancement direction may be selected so that the interventional tool may be delivered through a preferred access point while the practitioner operates from an ergonomic posture and position. In an exemplary embodiment, the advancement direction is between 30° and 180°, 45° and 135°, or 60° and 120° relative to the insertion axis, and in some exemplary embodiments is perpendicular to the insertion axis.

Operation 1006 may include viewing the patient and a monitor while advancing the interventional tool. For example, the support sheath may be selected and configured such that the monitor and access point are in a common field of vision of the practitioner during advancement of the interventional tool. In some embodiments, the insertion axis extends in a direction perpendicular to the viewable display of the monitor, and the proximal portion of the support sheath is oriented parallel to the viewable display of the monitor, during the step of advancing the interventional tool.

While this specification contains many specific implementation details, these should not be construed as limitations on the scope of any technology or of what may be claimed, but rather as descriptions of features that may be specific to particular embodiments. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Particular embodiments of the subject matter have been described. Other embodiments are within the scope of the following claims.

What is claimed is:

1. A medical sheath system, comprising:
   a support sheath comprising an inflexible tube comprising a first end having a connector configured to releasably connect with a proximal end of a catheter and a second end comprising a port configured to receive an interventional tool, the inflexible tube having a distal portion proximate the first end and a proximal portion proximate the second end,
   wherein the inflexible tube comprises a curve that defines a predetermined angle between the proximal portion of the support sheath and distal portion of the support sheath, the inflexible tube configured to maintain the predetermined angle while the interventional tool is moved through the support sheath and a patient access opening.

2. The medical sheath system of claim 1, further comprising a catheter having a distal end, a proximal end, and at least one lumen extending between the distal end and the proximal end, wherein the catheter is configured to receive the interventional tool and comprises a sealable connector at the proximal end having a septum.

3. The medical sheath system of claim 2, wherein the catheter is configured for insertion through an opening of a patient's skin, the lumen defining an insertion axis at the opening of the patient's skin.

4. The medical sheath system of claim 2, further comprising an adapter configured to join the first end of the catheter to the distal end of the inflexible tube.

5. The medical sheath system of claim 1, further comprising an extension sheath configured to be connected to the second end of the inflexible tube, at least a distal portion of the extension sheath oriented in the predetermined angle relative to the insertion axis when connected to the inflexible tube.

6. The medical sheath system of claim 1, wherein the inflexible tube is a first inflexible tube, the medical sheath system further comprising a second inflexible tube, the second inflexible tube comprising a first end having a connector and a second end comprising a port configured to receive the interventional tool, the second inflexible tube having a distal portion proximate the first end and a proximal portion proximate the second end.

7. The medical sheath system of claim 6, wherein the distal portion of the first inflexible tube is fixed in a predetermined orientation angled between 60° and 135° relative to the second proximal portion of the first inflexible tube.

8. The medical sheath system of claim 6, wherein the first inflexible tube and the second inflexible tube are interchangeably connectable with the catheter.

9. The medical sheath system of claim 1, further comprising a retainer configured to secure the support sheath to a surface or maintain a catheter in a stable position relative to the patient access opening.

10. The medical sheath system of claim 9, wherein the retainer comprises an elastic sleeve configured to secure the inflexible tube around an arm or leg.

11. The medical sheath system of claim 1, wherein the distal portion of the inflexible tube is fixed in a predetermined orientation perpendicular to the proximal end.

12. The medical sheath system of claim 1, wherein the predetermined angle is between 60° and 135°.

13. The medical sheath system of claim 1, wherein the interventional tool comprises a guidewire.

14. A medical sheath system, comprising:
   a support sheath comprising an inflexible tube comprising a first end having a connector configured to releasably connect with a proximal end of a catheter and a second end comprising a port configured to receive an interventional tool, the support sheath having a distal portion proximate the first end and a proximal portion proximate the second end, the distal portion fixed in a predetermined orientation relative to the proximal end; and
   a retainer configured to maintain the support sheath in a position relative to a patient access opening while the interventional tool is moved through the support sheath and a patient access opening such that the proximal portion is oriented along an insertion axis of the interventional tool through the patent access opening.

15. The medical sheath system of claim 14, wherein the support sheath comprises a curve that defines a predetermined angle between the proximal portion of the support sheath and distal portion of the support sheath.

16. The medical sheath system of claim 15, wherein the predetermined angle is between 60° and 135°.

17. The medical sheath system of claim 16, further comprising a catheter having a distal end, a proximal end, and at least one lumen extending between the distal end and the proximal end, wherein the catheter is configured to receive the interventional tool and comprises a sealable connector at the proximal end having a septum.

18. The medical sheath system of claim 14, further comprising an adapter configured to join the first end of the catheter to the distal end of the inflexible tube.

19. The medical sheath system of claim 14, further comprising an extension sheath configured to be connected to the second end of the inflexible tube, at least a distal portion of the extension sheath oriented in a predetermined angle relative to the insertion axis when connected to the inflexible tube.

20. The medical sheath system of claim 14, wherein the retainer comprises an elastic sleeve configured to secure the inflexible tube around an arm or leg.

* * * * *

UNITED STATES PATENT AND TRADEMARK OFFICE
CERTIFICATE OF CORRECTION

PATENT NO. : 11,517,721 B2
APPLICATION NO. : 16/786597
DATED : December 6, 2022
INVENTOR(S) : Gregory Gordon Page 1 of 1

It is certified that error appears in the above-identified patent and that said Letters Patent is hereby corrected as shown below:

On the Title Page

Item (54), Line 2, delete "MELHODS" and insert --METHODS--;

In the Specification

In Column 1, Line 2, in the Title, delete "MELHODS" and --METHODS--.

Signed and Sealed this
Twenty-fourth Day of January, 2023

Katherine Kelly Vidal
*Director of the United States Patent and Trademark Office*